(12) United States Patent
Farag

(10) Patent No.: US 9,415,104 B2
(45) Date of Patent: *Aug. 16, 2016

(54) COMBINATION THERAPY TO ENHANCE NK CELL MEDIATED CYTOTOXICITY

(71) Applicant: NOVO NORDISK A/S, Bagsvaerd (DK)

(72) Inventor: Sherif S. Farag, Carmel, IN (US)

(73) Assignee: Novo Nordisk A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 14/198,845

(22) Filed: Mar. 6, 2014

(65) Prior Publication Data
US 2014/0302052 A1 Oct. 9, 2014

Related U.S. Application Data

(62) Division of application No. 13/132,346, filed as application No. PCT/US2009/066894 on Dec. 4, 2009, now Pat. No. 8,709,411.

(60) Provisional application No. 61/120,242, filed on Dec. 5, 2008.

(51) Int. Cl.
| *A61K 39/395* | (2006.01) |
| *A61K 31/44* | (2006.01) |
| *A61K 31/45* | (2006.01) |
| *A61K 31/4439* | (2006.01) |
| *A61K 31/454* | (2006.01) |

(52) U.S. Cl.
CPC ......... *A61K 39/3955* (2013.01); *A61K 31/4439* (2013.01); *A61K 31/454* (2013.01); *A61K 39/395* (2013.01)

(58) Field of Classification Search
None
See application file for complete search history.

(56) References Cited

U.S. PATENT DOCUMENTS

8,709,411 B2 * 4/2014 Farag ................ A61K 31/4439
424/130.1
2006/0263361 A1 11/2006 Moretta et al.

FOREIGN PATENT DOCUMENTS

| WO | WO 2005/003172 | 1/2005 |
| WO | WO 2006/003179 | 1/2006 |
| WO | WO 2006/072625 | 7/2006 |
| WO | WO 2008/084106 | 7/2008 |

OTHER PUBLICATIONS

Aranda et al. (2014) OncoImmunology 3, e27297: 1-11.*
Benson et al. (2015) Clin Cancer Res; 21(18): 4055-4061.*
Segler et al. (2012) Cancer Chemother Pharmacol; 69: 1393-1406.*
Database Biosis [Online] Bioscienes Information Service, Accession No. PREV200800216192, Sutherland, M. et al. "SGN-33, lintuzumab, demonstrates anti-leukemic activity in preclinical models of AML" Nov. 2007, XP-002570331, pp. 1-2.
Database Biosis [Online] Bioscienes Information Service, Accession No. PREV200700260461, Wu, L. et al. "Lenalidomide strongly enhances natural killer (NK) cell mediated antibody-dependent cellular cytotoxicity (ADCC) of rituximab treated non-Hodkin's lymphoma cell lines in vitro" Nov. 2006, XP-002570332, pp. 1-2.
Zhang, S. et al. "#3245 Enhanced NK cell mediated cytotoxicity against multiple myeloma (MM) cells by the combination of anti-KIR (1-7F9) monoclonal antibody (mAb) and lenalidomide" Proceedings of the American Association for Cancer Research Annual Meeting, Apr. 18-22, 2009, pp. 785-786, vol. 50.
Wu et al. "lenalidomide enhances natural killer cell and monocyte-mediated antibody-dependent cellular cytotoxicity of rituximab-treated CD20+ tumor cells," Clin Cancer Res. Jul. 15, 2008;14(14):4650-7.
List et al. "Lenalidomide in the myelodysplastic syndrome with chromosome 5q deletion," N Engl J Med. Oct. 5, 2006;355(14):1456-65.
Dimopoulos et al. "Study of Lenalidomide Plus Dexamethasone Versus Dexamethasone Alone in Relapsed or Refractory Multiple Myeloma (MM): Results of a Phase 3 Study (MM-010)," Blood (ASH Annual Meeting Abstracts) 2005 106: Abstract 6, p. 6A-7A.
Witzig et al., "Early Results from a Phase II Study of Lenalidomide Monotherapy in Relapsed/Refractory Indolent Non-Hodgkin's Lymphoma," Blood (ASH Annual Meeting Abstracts) 2006 108: Abstract 2482, p. 703A.
Bartlett et al. "The evolution of thalidomide and its IMiD derivatives as anticancer agents,".Nat Rev Cancer. Apr. 2004;4(4):314-22.
Wagtman, N., et al. "Anti-KIR (1-7F9): A Fully Human Monoclonal Antibody (mAb) That Blocks KIR2DL1, —2 and —3, Promoting Natural Killer (NK) Cell-Mediated Lysis of Tumor Cells In Vitro and In Vivo," Blood (ASH Annual Meeting Abstracts), Nov. 2007; 110: 582.
Benson, D. et al., "IPH2101, a novel anti-inhibitory KIR antibody, and lenalidomide combine to enhance the natural killer cell versus multiple myeloma effect," Blood. Dec. 8, 2011;118(24):6387-91.

* cited by examiner

*Primary Examiner* — Ilia Ouspenski
(74) *Attorney, Agent, or Firm* — LeClairRyan, a professional organization; Robin L. Teskin

(57) ABSTRACT

The function of natural killer (NK) cells is regulated by inhibitory and activating signals delivered by cell surface receptors, 1-7F9 is a fully human monoclonal antibody (mAb) directed against KIR2DL1 and K1R2DL2/3 receptors that blocks its interaction with its HLA-C ligands breaking NK cell tolerance to autologous tumor ceils. Lenalidomide has been shown to increase NK cell cytotoxicity in vitro. The combination of lenalidomide and 1-7F9 enhanced NK cell mediated cytotoxicity against U266 cells beyond that observed with each agent alone. Lenalidomide also increased the expression of NKG2D, DNAM-I and TRAIL ligands including: MICA, ULB P2, CD1 12 and DR 4 on U266 cells. In in vitro cytotoxicity assays, lenalidomide enhanced the susceptibility of myeloma cell lines to NK ceil. The NK ceil signaling pathways was also explored after lenalidomide treatment and the results show that lenalidomide may upregulate the phospho-SHIP1 (Tyr1020) and has no effect on phospho-p44/42 (ERK 1/2) (Thr202/Tyr204) in NK cells. These results provide pre¬ clinical rationale for clinical investigation of 1-7F9 anti-KIR mAb and lenalidomide in MM.

23 Claims, 13 Drawing Sheets

SEQUENCE LISTING

```
<160> NUMBER OF SEQ ID NOS: 3

<210> SEQ ID NO 1
<211> LENGTH: 109
<212> TYPE: PRT
<213> ORGANISM: Homo sapiens

<400> SEQUENCE: 1

Glu Ile Val Leu Thr Gln Ser Pro Val Thr Leu Ser Leu Ser Pro Gly
```

```
                 1               5                  10                 15
            Glu Arg Ala Thr Leu Ser Cys Arg Ala Ser Gln Ser Val Ser Ser Tyr
                            20                  25                 30

Leu Ala Trp Tyr Gln Gln Lys Pro Gly Gln Ala Pro Arg Leu Leu Ile
                        35                  40                  45

Tyr Asp Ala Ser Asn Arg Ala Thr Gly Ile Pro Ala Arg Phe Ser Gly
                    50                  55                  60

Ser Gly Ser Gly Thr Asp Phe Thr Leu Thr Ile Ser Ser Leu Glu Pro
            65                  70                  75                  80

Glu Asp Phe Ala Val Tyr Tyr Cys Gln Gln Arg Ser Asn Trp Met Tyr
                            85                  90                  95

Thr Phe Gly Gln Gly Thr Lys Leu Glu Ile Lys Arg Thr
                            100                 105

<210> SEQ ID NO 2
<211> LENGTH: 123
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
            1               5                   10                  15

Ser Val Lys Val Ser Cys Lys Ala Ser Gly Gly Thr Phe Ser Phe Tyr
                            20                  25                  30

Ala Ile Ser Trp Val Arg Gln Ala Pro Gly Gln Gly Leu Glu Trp Met
                        35                  40                  45

Gly Gly Phe Ile Pro Ile Phe Gly Ala Ala Asn Tyr Ala Gln Lys Phe
                    50                  55                  60

Gln Gly Arg Val Thr Ile Thr Ala Asp Glu Ser Thr Ser Thr Ala Tyr
            65                  70                  75                  80

Met Glu Leu Ser Ser Leu Arg Ser Asp Asp Thr Ala Val Tyr Tyr Cys
                            85                  90                  95

Ala Arg Ile Pro Ser Gly Ser Tyr Tyr Tyr Asp Tyr Asp Met Asp Val
                            100                 105                 110

Trp Gly Gln Gly Thr Thr Val Thr Val Ser Ser
                        115                 120

<210> SEQ ID NO 3
<211> LENGTH: 469
<212> TYPE: PRT
<213> ORGANISM: Homo sapiens
<220> FEATURE:
<221> NAME/KEY: SIGNAL
<222> LOCATION: (1)..(8)

<400> SEQUENCE: 3

Met Asp Trp Thr Trp Arg Phe Leu Phe Val Val Ala Ala Ser Thr Gly
            1               5                   10                  15

Val Gln Ser Gln Val Gln Leu Val Gln Ser Gly Ala Glu Val Lys Lys
                            20                  25                  30

Pro Gly Ser Ser Val Lys Val Ser Cys Lys Ala Ser Gly Gly Thr Phe
                        35                  40                  45

Ser Phe Tyr Ala Ile Ser Trp Val Arg Gln Ala Pro Gly Gln Gly Leu
                    50                  55                  60

Glu Trp Met Gly Gly Phe Ile Pro Ile Phe Gly Ala Ala Asn Tyr Ala
            65                  70                  75                  80

Gln Lys Phe Gln Gly Arg Val Thr Ile Thr Ala Asp Glu Ser Thr Ser
```

```
                        85                  90                  95
Thr Ala Tyr Met Glu Leu Ser Ser Leu Arg Ser Asp Thr Ala Val
            100                 105             110
Tyr Tyr Cys Ala Arg Ile Pro Ser Gly Ser Tyr Tyr Asp Tyr Asp
            115             120             125
Met Asp Val Trp Gly Gln Gly Thr Thr Val Thr Val Ser Ser Ala Ser
    130                 135                 140
Thr Lys Gly Pro Ser Val Phe Pro Leu Ala Pro Cys Ser Arg Ser Thr
145                 150                 155                 160
Ser Glu Ser Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
        195                 200                 205
Ser Val Val Thr Val Pro Ser Ser Ser Leu Gly Thr Lys Thr Tyr Thr
    210                 215                 220
Cys Asn Val Asp His Lys Pro Ser Asn Thr Lys Val Asp Lys Arg Val
225                 230                 235                 240
Glu Ser Lys Tyr Gly Pro Pro Cys Pro Pro Cys Pro Ala Pro Glu Phe
                245                 250                 255
Leu Gly Gly Pro Ser Val Phe Leu Phe Pro Pro Lys Pro Lys Asp Thr
                260                 265                 270
Leu Met Ile Ser Arg Thr Pro Glu Val Thr Cys Val Val Val Asp Val
            275                 280                 285
Ser Gln Glu Asp Pro Glu Val Gln Phe Asn Trp Tyr Val Asp Gly Val
    290                 295                 300
Glu Val His Asn Ala Lys Thr Lys Pro Arg Glu Gln Phe Asn Ser
305                 310                 315                 320
Thr Tyr Arg Val Val Ser Val Leu Thr Val Leu His Gln Asp Trp Leu
            325                 330                 335
Asn Gly Lys Glu Tyr Lys Cys Lys Val Ser Asn Lys Gly Leu Pro Ser
                340                 345                 350
Ser Ile Glu Lys Thr Ile Ser Lys Ala Lys Gly Gln Pro Arg Glu Pro
        355                 360                 365
Gln Val Tyr Thr Leu Pro Pro Ser Gln Glu Met Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Arg Leu
            420                 425                 430
Thr Val Asp Lys Ser Arg Trp Gln Glu Gly Asn Val Phe Ser Cys Ser
        435                 440                 445
Val Met His Glu Ala Leu His Asn His Tyr Thr Gln Lys Ser Leu Ser
    450                 455                 460
Leu Ser Leu Gly Lys
465
```

COMBINATION THERAPY TO ENHANCE NK CELL MEDIATED CYTOTOXICITY

PRIORITY CLAIM

This application is a division of U.S. application Ser. No. 13/132,346, filed Aug. 15, 2011, now U.S. Pat. No. 8,709,411, which is a National Stage Entry of PCT Application No. PCT/US2009/066894, which claims the benefit of U.S. provisional patent application No. 61/120,242 filed on Dec. 5, 2008, all of which are herein incorporated by reference in their entirety.

SEQUENCE LISTING

The sequence listing in the file named "43271o3802" having a size of 6,595 bytes that was created Nov. 10, 2015 is hereby incorporated by reference in its entirety.

FIELD OF THE INVENTION

This invention relates generally to, methods of enhancing natural killer cell mediated cytotoxicity of tumor cells by the combination of anti-KIR mAB (1-7F9) monoclonal antibody and immunomodulatory agents, such as lenalidomide (3-(4-amino-1-oxo-1,3 dihydro-isoindol-2-yl)piperidine-2,6-dione).

BACKGROUND

Natural killer cells (NK cells) are a component of the innate immune system. These cells are classified as cytotoxic lymphocytes. These cells are unique and different to other cells of the immune cells in that they do not require prior exposure to antigen and do not have receptors for recognition of specific antigen sequences. Rather, NK cells express activating and inhibitory receptors that recognize ligands on target cells, with activation of NK cells dependent on the balance of activating and inhibitory signals mediated by these receptors. Importantly, NK cells express killer immunoglobulin-like receptors (KIR) that are inhibited by Class I major histocompatibility (MHC) markers on target cells. Transformed or virally infected cells downregulate MHC class I molecules and are therefore susceptible to killing by NK cells. In an normally functioning immune system NK cells play a primary role in the destruction of many types of tumor cells and various human cells of infected by viruses. NK cells induce apoptosis in target cells by releasing various factors in to the target cells that activate the cells own apoptotic pathway.

Given the recalcitrance of many tumor cells to all known therapies to treat cancer and the adverse side effects associated with even many of the best therapies to treat cancer there remains a profound need for new compounds and methods to treat cancerous tumors. Some aspects of the invention seek to address these needs.

SUMMARY

Some aspects of the invention include methods of killing cells comprising the steps of providing a biologically active amount of 3-(4-amino-1-oxo-1,3 dihydro-isoindol-2-yl)piperidine-2,6-dione or a pharmaceutically acceptable salt thereof; supplying a biologically active amount of an anti-KIR antibody or biologically active fragment thereof; and contacting said 3-(4-amino-1-oxo-1,3 dihydro-isoindol-2-yl)piperidine-2,6-dione and said anti-KIR antibody or biologically active fragment thereof, with a cell.

In some embodiment the anti-KIR antibody is 1-7F9, or a biologically active fragment thereof. In some embodiments the cells are cancer cells including for example myeloma cells, lymphoma cells, leukemia cells, and U266 cells.

In some embodiments the biologically active amount of 3-(4-amino-1-oxo-1,3 dihydro-isoindol-2-yl)piperidine-2,6-dione is less than or equal to 10 $\mu molL^{-1}$. In some embodiments the biologically active amount of 1-7F9 is equal to or less than 30 ug/ml, or an amount known to saturate KIR receptors on NK cells. Still other aspects of the invention include methods of treating a patient, comprising the steps of: providing a therapeutically effective amount of 3-(4-amino-1-oxo-1,3 dihydro-isoindol-2-yl)piperidine-2,6-dione or a pharmaceutically acceptable salt thereof; supplying a therapeutically effective amount of an anti-KIR antibody, or a fragment thereof; and administering said therapeutically effective amounts of said lenalidomide and anti-KIR antibody to a patient in need thereof. In some embodiments the anti-KIR antibody is the monoclonal antibody 1-7F9. In some embodiments the patient is either a human being or a non-human animal. In one aspect, the patient to be treated by the above-described method is a patient diagnosed with cancer, e.g. a myeloma, a leukemia, a lymphoma. In a more particular aspect, the patient is a patient diagnosed with multiple myeloma (MMy). In another particular aspect, the patient is a patient diagnosed with chronic myeloid leukaemia (CML). In still another particular aspect, the patient is a patient diagnosed with acute myeloid leukaemia (AML). In another particular aspect, the patient is a patient diagnosed with chronic lymphocytic leukemia (CLL) or small lymphocytic lymphoma (SLL), or a myelodysplastic syndrome.

In some embodiments, the therapeutically effective amount of 3-(4-amino-1-oxo-1,3 dihydro-isoindol-2-yl)piperidine-2,6-dione or a pharmaceutically acceptable salt thereof, is between about 1 mg to about 50 mg per day. In still other embodiments the therapeutically effective amount of 3-(4-amino-1-oxo-1,3 dihydro-isoindol-2-yl)piperidine-2,6-dione or a pharmaceutically acceptable salt thereof, is between about 1 mg to about 50 mg per day. While in still other embodiments the therapeutically effective amount of 3-(4-amino-1-oxo-1,3 dihydro-isoindol-2-yl)piperidine-2,6-dione or a pharmaceutically acceptable salt thereof, is between about 5 mg to about 50 mg per day. And in still other embodiments the therapeutically effective amount of 3-(4-amino-1-oxo-1,3 dihydro-isoindol-2-yl)piperidine-2,6-dione or a pharmaceutically acceptable salt thereof, is between about 1 mg to about 25 mg per day.

In some embodiments the therapeutically effective amount of 1-7F9 is between about 1 mg/kg to about 3 mg/kg per month. In still other embodiments the therapeutically effective amount of 1-7F9 is between about 1 mg/kg of the patient's body weight to about 3 mg/kg per month.

Still other aspects of the invention include kits for inducing cell death, comprising: a biologically active amount of 3-(4-amino-1-oxo-1,3 dihydro-isoindol-2-yl)piperidine-2,6-dione or a pharmaceutically acceptable salt thereof; and a biologically active amount of an anti-KIR antibody or biologically active fragment thereof. In some embodiments the anti-KIR antibody in the kit is 1-7F9.

Yet other aspects of the invention include kits for inducing for treating a disease, comprising: at least one therapeutically effective dose of 3-(4-amino-1-oxo-1,3 dihydro-isoindol-2-yl)piperidine-2,6-dione or a pharmaceutically acceptable salt thereof; and at least one therapeutically effective dose of an anti-KIR antibody or biologically active fragment thereof. In some embodiment the anti-KIR antibody in the kit is 1-7F9.

DESCRIPTION

Figure 1:
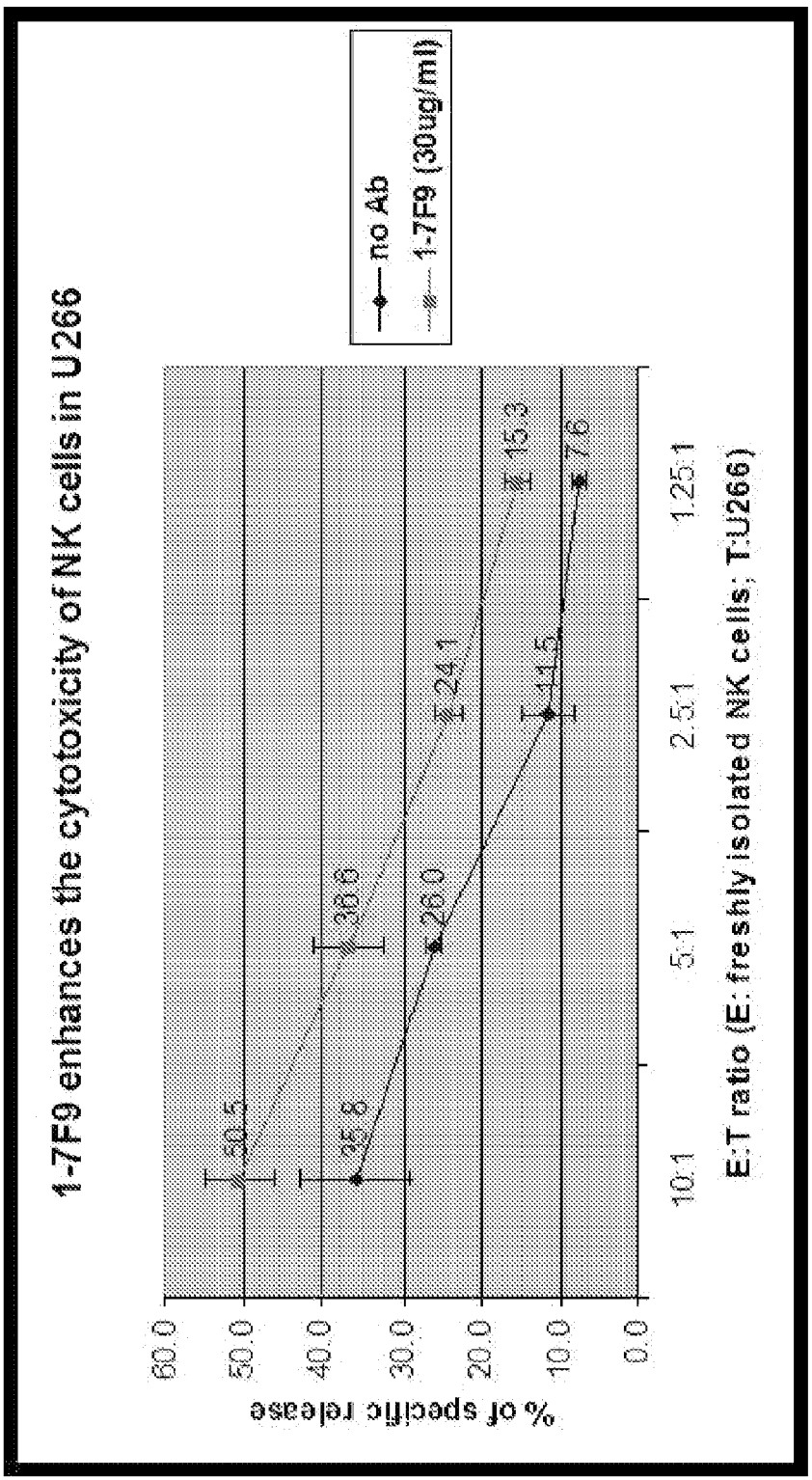
FIG. 1. Graph illustrating the effect of different effector (E:NK cells) to tumor target (T) ratios (E:T ratios) on the percent of specific release.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

As used herein, unless stated otherwise the term 'about' means plus or minus 10 percent, e.g. about 1 encompasses values ranging from 0.9 to 1.1.

As used herein unless stated otherwise, the terms, 'biologically active amounts' or 'biologically active doses,' mean amounts or doses capable of induce a noticeable effect on cells or cellular components after either a single dose or multiple doses of the compounds.

As used herein unless stated otherwise, the term, 'therapeutically effective amounts' or ' therapeutically effective doses,' mean amounts or doses capable of producing a beneficial effect on a human or animal after either a single or multiple treatments with the compounds.

Tumor cells that express normal levels of MHC class I molecules may be resistant to killing by autologous NK cells because of inhibitory signals mediated by the interaction of inhibitory KIR with MHC class I ligands.

The anti-KIR antibody 1-7F9 blocks the interaction of KIR and MHC class I molecules and enhances susceptibility to killing by autologous NK cells and is being developed for clinical anti-cancer therapy. The anti-KIR antibodies used according to the invention reduce KIR mediated inhibition of NK cells. Other anti-KIR antibodies may bind and block the signaling activity of inhibitory KIRs including one or more members of the KIR2DL subfamilies. Inhibitory KIRs having two Ig domains (KIR2DL) recognize HLA-C allotypes: KIR2DL2 (formerly designated p58.2) and the closely related, allelic gene product KIR2DL3 both recognize "group 1" HLA-C allotypes (including HLA-Cw1, -3, -7, and -8), whereas KIR2DL1 (p58.1) recognizes "group 2" HLA-C allotypes (such as HLA-Cw2, -4, -5, and -6). The recognition by KIR2DL1 is dictated by the presence of a Lys residue at position 80 of HLA-C alleles. KIR2DL2 and KIR2DL3 recognition is dictated by the presence of an Asn residue at position 80 in HLA-C. Importantly, the great majority of HLA-C alleles have either an Asn or a Lys residue at position 80. Therefore, KIR2DL1, -2, and -3 collectively recognize essentially all HLA-C allotypes found in humans. Determining whether an antibody reduces KIR mediated inhibition can be tested by standard methods such as in a chromium assay with an NK cell clone expressing one or several KIRs, and a target cell expressing only one HLA allotype recognized by one of the KIR of the NK clone and no other HLA class I molecule recognized by the other KIRs on the NK clone, the level of cytotoxicity obtained with the antibody should be at least 60% preferably at least 70%, or more of the cytotoxicity obtained with a control antibody that blocks the interactions between KIR and HLA-C. WO2005003172, WO2005003168, and WO2005009465, each of which is herein incorporated by reference in its entirety, describe KIR2DL1 and KIR2DL2/3 cross-reactive antibodies such as, e.g., DF200, 1-7F9, 1-4F1, 1-6F5, and 1-6F1, and that DF200 and 1-7F9 enhance NK cell cytotoxicity. Other anti-KIR antibodies include GL183 and EB6 available from (Beckman Coutler or Immunotech, France). Any of these antibodies or antibodies that compete with these for binding a KIR polypeptides and block KIR signaling can be used.

Doses of anti-KIR antibodies are described, for example, in WO/2008/084106 which is herein incorporated by reference in its entirety. Optionally, the dose of anti-KIR antibody is in the range from about 0.0003 to about 3 mg/kg; from about 0.003 to about 3 mg/kg; from about 0.015 to about 3 mg/kg; from about 0.075 to about 3 mg/kg; from about 0.075 to about 3 mg/kg; from about 0.3 to about 3 mg/kg, and from about 1 to about 3 mg/kg. Exemplary doses are about 0.0003, about 0.003, about 0.015, about 0.075, about 0.3, about 1, and about 3 mg/kg.

Immunomodulatory agents (e.g., lenalidomide, thalidomide, and other analogues) enhance NK cell function and number in vitro and in vivo and have significant activity against a variety of cancers through a number of mechanisms. Given the ability of immunomodulatory agents to enhance NK cells activity, they may work synergistically with anti-KIR antibody to enhance immunological attack on cancer cells. The combination of immunomodulatory agents and anti-KIR may represent a novel immunotherapy approach for a variety of different cancers.

The function of natural killer (NK) cells is regulated by inhibitory and activating signals delivered by cell surface receptors. Interaction of 'self' MHC class I molecules with inhibitory receptors expressed on the surface of NK cells inhibits NK cell-mediated cytotoxicity against autologous cancer cells. 1-7F9 is a human monoclonal antibody (mAb) directed against KIR2DL1, -2 and -3 receptors that blocks their interaction with HLA-C ligands, thereby breaking the NK cell's tolerance of autologous tumor cells. The mAb 1-7F9 is currently undergoing clinical investigation as a single agent in phase I trials in multiple myeloma (MM) and acute myeloid leukemia.

For an additional discussion of the bio-synthesis, isolation, characterization and uses for the monoclonal antibody 1-7F9 and various bioactive fragments, derivatives and formulations thereof the reader is directed to various publications, including, but not limited to, U.S. application Ser. No. 11/324,356 filed on Jan. 3, 2006, which published on Dec. 14, 2006 as publication number US2006/0280740 a corrected version of which was published on Jul. 30, 2009 as publication number US2009/0191213A9, each of which is herein incorporated by reference in its entirety as if each were separately incorporated by reference in its entirety.

The compound lenalidomide is highly effective in the clinical treatment of MM, and has also been shown to increase NK cell cytotoxicity in vitro. This compound is available commercially and sold under the trade names Revlimid® and Revimid®. For an additional discussion of the synthesis, isolation, characterization and uses of lenalidomide and its analogs, derivatives, formulations, pharmaceutically acceptable salts and bio-available crystal forms thereof, the reader is directed to various publications, including, but not limited to, U.S. Pat. No. 5,635,517 filed on Jul. 24, 1996; U.S. Pat. No. 6,045,501 filed on Aug. 28, 1998; U.S. Pat. No. 6,281,230 filed on Apr. 15, 2000; U.S. Pat. No. 6,315,720 filed Oct. 23, 2000; U.S. Pat. No. 6,555,554 filed on Feb. 12, 2001; U.S. Pat. No. 6,561,976 filed on Sep. 26, 2001; U.S. Pat. No. 6,561,977 filed on Sep. 27, 2001; U.S. Pat. No. 6,755,784 filed on Mar. 7, 2003, U.S. Pat. No. 6,908,432 filed on Jan. 22, 2004; U.S. Pat. No. 7,119,106 filed Jan. 6, 2003, U.S. Pat. No. 7,189,740 filed Apr. 11, 2003, and U.S. Pat. No. 7,465,800 filed Sep. 3, 2004, each of which is herein incorporated by reference in its entirety. Lenalidomide has been investigated in a variety of conditions, including B-cell cancer (e.g. multiple myeloma (MM)), a leukemia, a lymphoma, chronic lymphocytic leukemia (CLL) or small lymphocytic lymphoma (SLL), myelodysplastic syndromes (e.g. associated with the chromosome 5 abnormality).

The potential for synergy between lenalidomide and 1-7F9 against cancer cells such as MM cells was investigated. Europium release cytotoxicity assays show that 1-7F9 blocking enhances NK cell mediated cytotoxicity against the relatively resistant MM U266 cells. U266 cells co-express groups 1 and 2 HLA-C class I ligands and are thus capable of inhibiting NK cells found in the majority of donors. The monoclonal antibody 1-7F9 significantly enhanced natural cytotoxicity against U266 cells of both purified NK cells at Effector:Target (E:T) ratios of 10:1 or less, and also of freshly isolated peripheral blood mononuclear cells (PBMC) at E:T ratios of 60:1 or less, from more than 10 random donors. In addition, treatment of PBMC with 10 $\mu molL^{-1}$ lenalidomide for 72 hours with or without interleukin (IL)-2 increased NK cell induced lysis of U266 cells. Finally, the combination of lenalidomide and 1-7F9 enhanced NK cell mediated cytotoxicity against U266 cells beyond that observed with each agent alone indicating a synergistic, or at least an additive effect.

Referring now to FIG. 1. Graph illustrating the effect of different effector (E: NK cells) to tumor target (T) ratios (E:T ratios) on the percent of specific release (killing of tumor target cells measured in the presence and absence of 30 $\mu g$ $ml^{-1}$ of the antibody 1-7F9. 1-7F9 enhances the cytotoxicity of NK cells against U266. No Ab vs 1-7F9: 10:1, p=0.0353; 5:1, p=0.0129; 2.5:1, p=0.0049; 1.25:1, p=0.0019.

Figure 2:
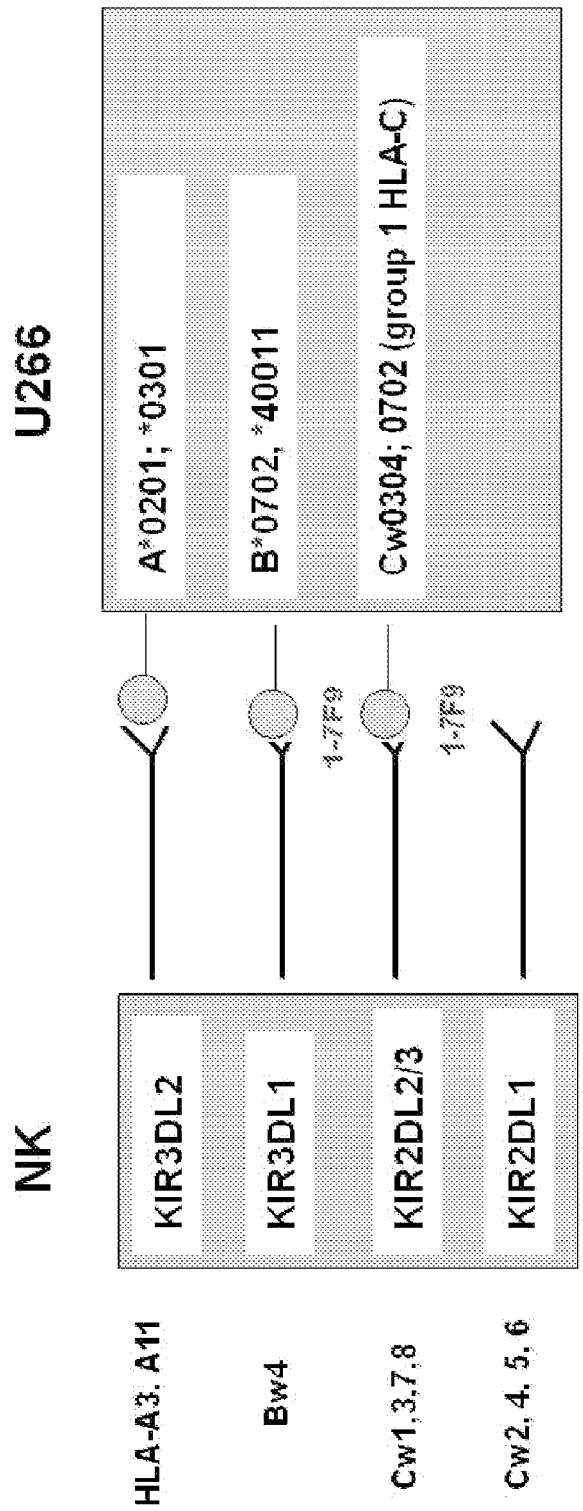
FIG. 2. Schematic illustrating the interaction between NK cells and U266 cells.

Referring now to FIG. 2. Schematic illustrating the interaction between NK cells and U266 cells. This schematic illustrates that the MM cell line U266 expresses both groups 1 and group 2 MHC class molecules; HLA-A, HLA-B, and group 1 HLA-C ligands on the cell surface which inhibit KIR2DL1 and KIR2D12/3 which are blocked by the anti-KIR antibody 1-7F9. Briefly, KIR2DL2 and KIR2DL3 bind to HLA-C* 0304 and HLA-C* 0702 and then block the NK cytotoxicity. 1-7F9 is monoclonal antibody against KIR2DL2/3 that block the interaction of KIR2DL2/3 with HLA-Cw3 or similar allotypes then increases the NK cytotoxicity.

Figure 3:
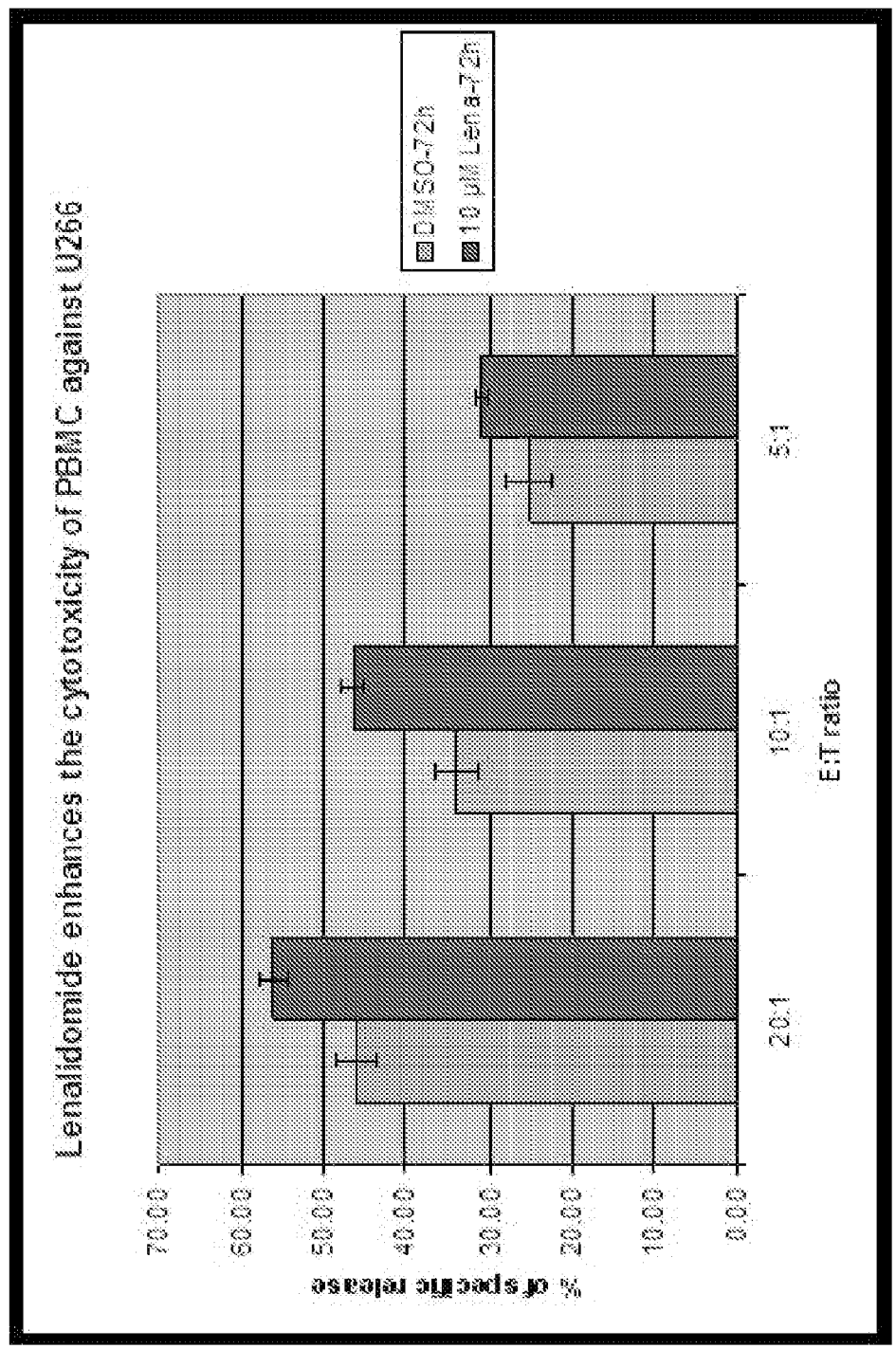
FIG. 3. Bar graph illustrating the effect of lenalidomide (10 μM) on enhancing killing of U266 cells by normal donor peripheral blood mononuclear cells (PBMC) at different E:T ratios.

Referring now to FIG. 3, Effector cells: PBMC were treated with DMSO or 10 $\mu molM$-1 lenalidomide for 72 h without IL-2. The target cells were U266 cells. Still referring to FIG. 3, a bar graph illustrating the effect of lenalidomide (10 $\mu M$) on enhancing killing of U266 cells by normal donor peripheral blood mononuclear cells (PBMC) at different E:T ratios as measured by the percent of specific release in a Europium release cytotoxicity assay. Lysis of U266 target cells is measured in the presence and absence of 10 $\mu M$ lenalidomide. The enhanced cytotoxicity of PBMC against U266 by lenalidomide occurred without adding interleukin (IL)-2 to the culture. The total NK cell numbers was essentially the same in the culture with DMSO treatment and in the culture with 10 $\mu mol/L$ lenalidomide treatment. Accordingly, differences in the number of NK cells does not account for why lenalidomide enhances the NK cytotoxicity.

Figure 4:
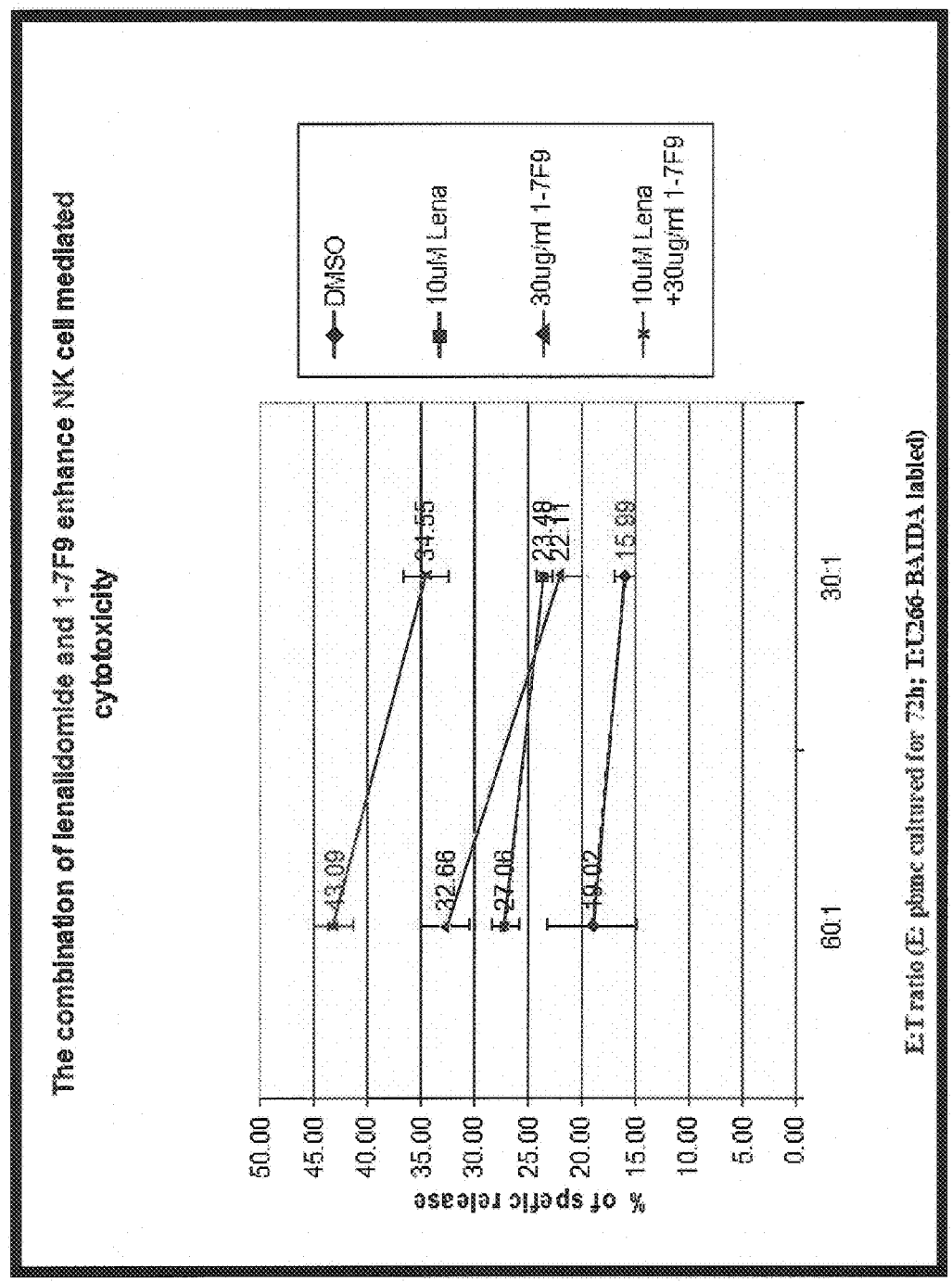
FIG. 4. Graph illustrating enhanced NK cell mediated cytotoxicity of U266 human myeloma cells by the combination of 1-7F9 and lenalidomide.

Referring now to FIG. 4. Peripheral blood mononuclear cells (PBMC) were obtained from normal donors following a Ficoll gradient separation. These cells were incubated for 72 hours in lenalidomide (10 $\mu molL^{-1}$) or DMSO as control, and then used as effector cells against U266 target cells in the presence or absence of 1-7F9 blocking antibody in Europium release cytotoxicity assays. Cytotoxicity assays were performed in the presence or absence of 30 $\mu g/ml$ 1-7F9. In experiments investigating the combination, PBMC were treated with lenalidomide (10 $\mu molL^{-1}$) or DMSO (control) for 72 hours, and then used as effector cells in the presence or absence of 1-7F9 (30 $\mu gml^{-1}$) in europium release assay. At an E:T ratio of 60:1, 30 $\mu g/ml$ 1-7F9 augmented specific lysis of U266 cells from 19±4% for DMSO-treated control PBMC to 32±2.2% (P=0.01). Lenalidomide (10 $\mu molL^{-1}$) enhanced specific cell lysis to 27±1.3% relative to control (P0.03), while the combination of lenalidomide (10 $\mu mol/L$) and 1-7F9 (30 $\mu g/ml$) resulted in specific cell lysis of 43±1.9%, which was significantly higher than lenalidomide alone (P=0.0003) or 1-7F9 mAb alone (P=0.003) (FIG. 4).

Still referring to FIG. 4, the combination of lenalidomide and 1-7F9 enhanced NK cell mediated cytotoxicity against U266 cells. At 60:1 ratio: DMSO vs Lena, p=0.0343; DMSO vs 1-7F9, p=0.01; DMSO vs (Lena+1-7F9), p=0.0008; Lena vs Lena+1-7F9; 0.0003; 1-7F9 vs Lena+1-7F9, p=0.0031. At 30:1 ratio: DMSO vs Lena, p=0.0006; DMSO vs 1-7F9, p=0.0098; DMSO vs (Lena+1-7F9 (, p=0.0002; Lena vs Lena+1-7F9, 0.0011; 1-7F9 vs Lena+1-7F9, p=0.0019. These results show that the combination of 1-7F9 anti-KIR mAb and lenalidomide have efficacy against other tumor types where lenalidomide might also exhibit activity. Accordingly, this combination provides of a method for treating cancers such as non-Hodgkin's lymphoma and the like.

Still referring to FIG. 4. As shown, U266 are relatively resistant to NK cell mediated killing (dark blue curve). 1-7F9 enhances the killing of U266, as does pre-incubation of PBMC with lenalidomide. Treatment with lenalidomide enhanced cytotoxicity of NK cells against U266 cells. Similarly, the use of 1-7F9 blocking anti-KIR antibody facilitated the killing of U266 cells. However, the combination of treatment of PBMC with lenalidomide and the use of 1-7F9 acts synergistically to enhance killing of U266 compared to either lenalidomide or 1-7F9 alone.

Figure 5:
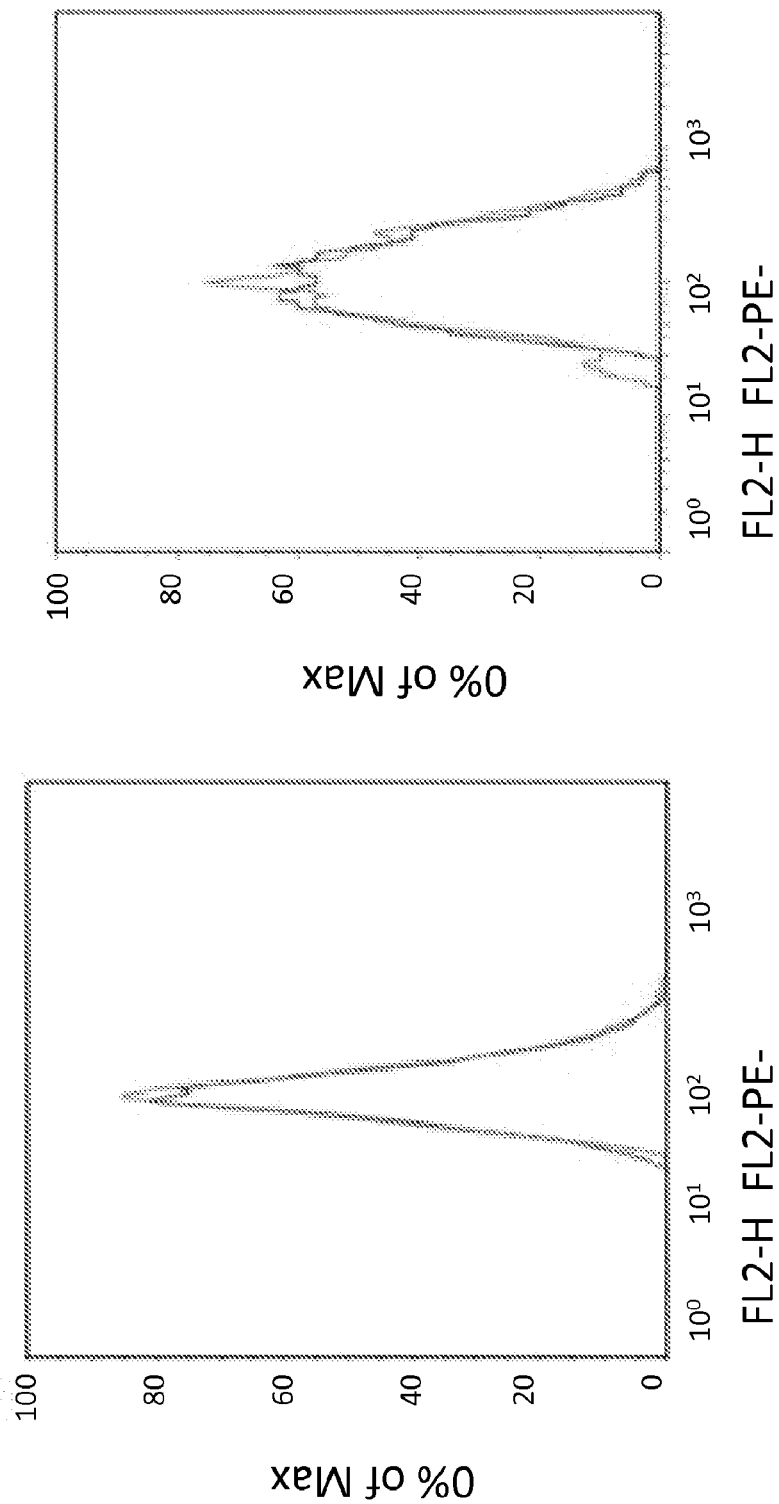
FIG. 5. Assays measuring the effect of treating purified NK cells with either lenalinomide in DMSO (light lines) or DMSO alone (dark lines) on the expression levels of the NK cell receptors NKG2D, NKG2A, KIR2DL1/S1, and KIRDL2/L3.
Figure 5:
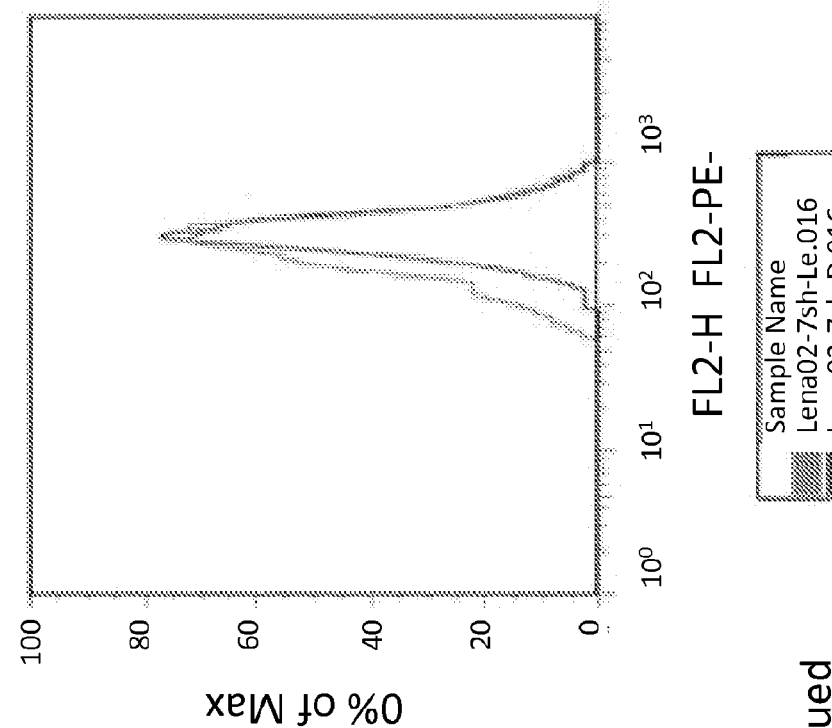
Figure 5:
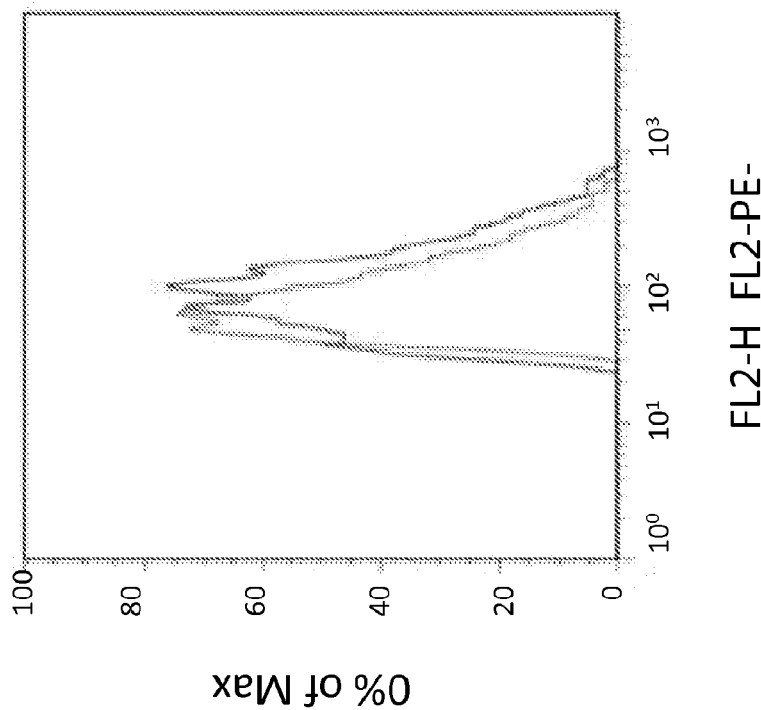

Referring now to FIG. 5. NK cells were purified from buffy coats of normal blood donors by immunomagnetic selection (CD3 depletion followed by CD56 selection) using the autoMACS (Milteny Biotec, Auburn, Calif.). Purified NK cells were cultured in RPMI medium with 10% human AB serum for 72 hours in the presence or absence of lenalidomide. NK cells were then assayed for receptor expression by flow-cytometry. As shown, lenalidomide has no effect on NK cell receptor expression indicating that its ability to enhance NK cell mediated lysis in combination with 1-7F9 is not related to upregulation of activating receptors (NKG2D) or downregulation of inhibitory receptors (NKG2A, KIR2DL1 or KIR2DL2/3). The levels of NK cells receptors expression were not significantly changed by treatment with lenalidomide.

Figure 6:
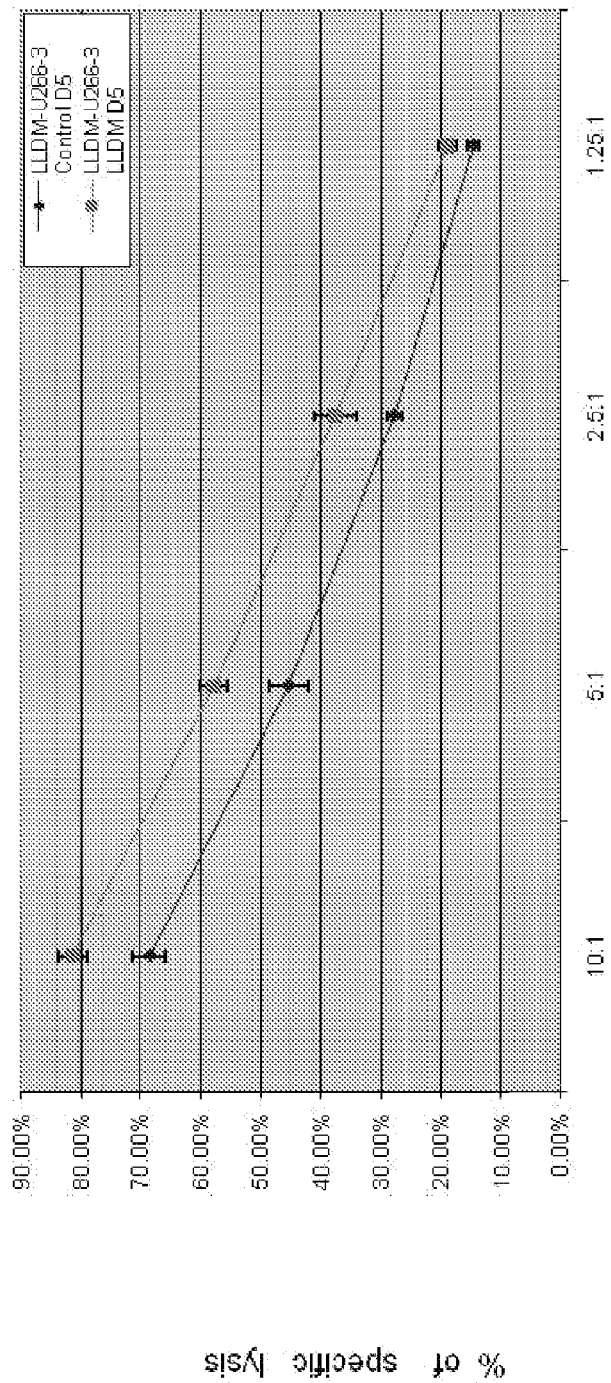
FIG. 6. Graph illustrating the effect of pre-incubating U266 target cells with lenalidomide on their susceptibility to lysis by fresh donor NK cells at different E:T ratios.

Referring now to FIG. 6. U266 cells were cultured in RPMI medium with 10% human AB serum (complete medium) in the presence or absence of lenalidomide (5 □M) for 5 days, and then used as target cells in Europium release cytotoxicity assays. As shown, U266 cells cultured in the presence of lenalidomide (pink curve) were more susceptible to lysis compared to U266 not exposed to lenalidomide (blue curve), indicating that lenalidomide may mediate its effect largely by enhancing susceptibility of target cells to NK mediated lysis. These results indicate that lenalidomide enhances the susceptibility of myeloma cell lines to NK cells in vitro.

Figure 7:
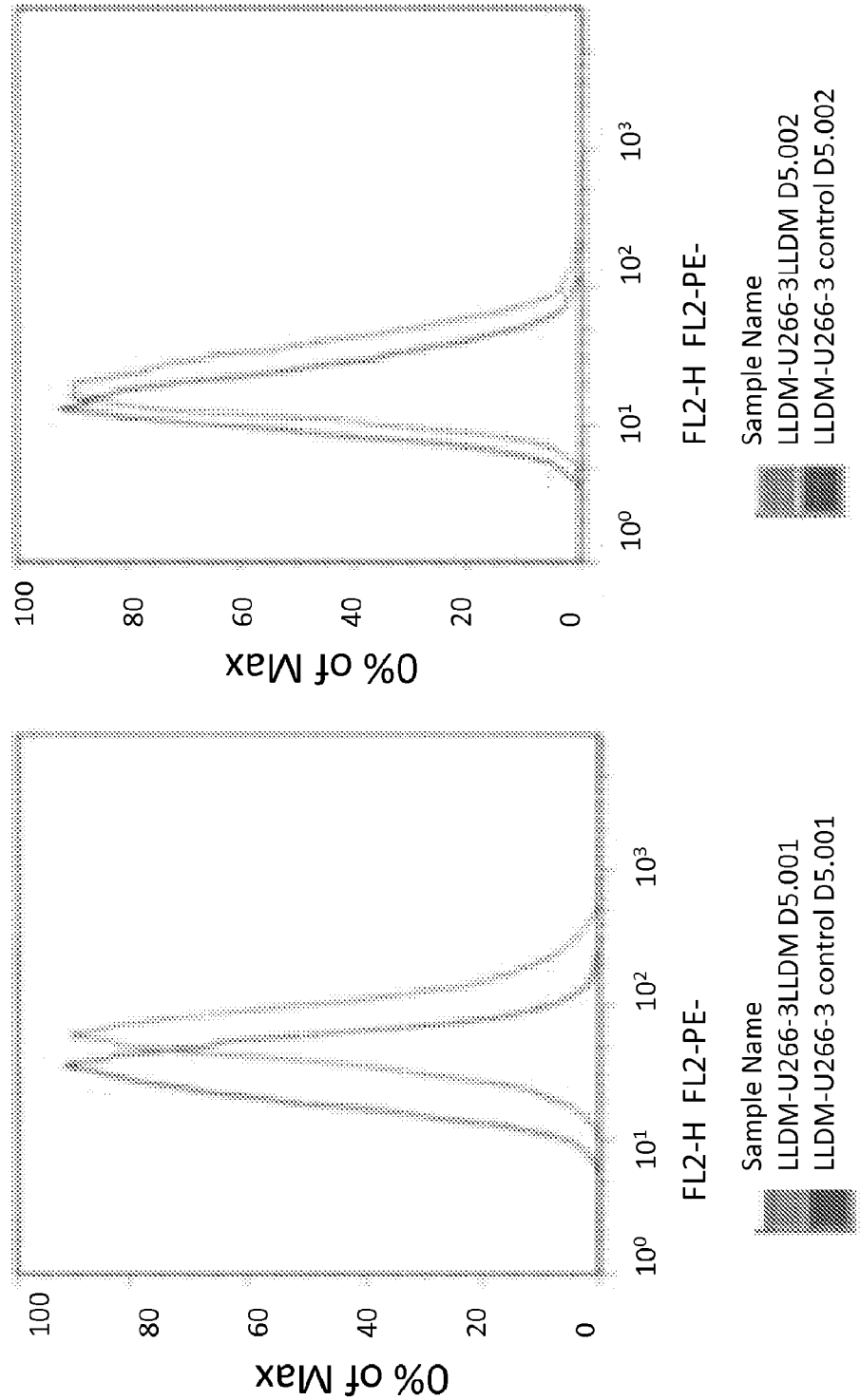
FIG. 7. Results for a representative experiment showing that lenalidomide increases the expression of activating ligands on target cells.
Figure 7:
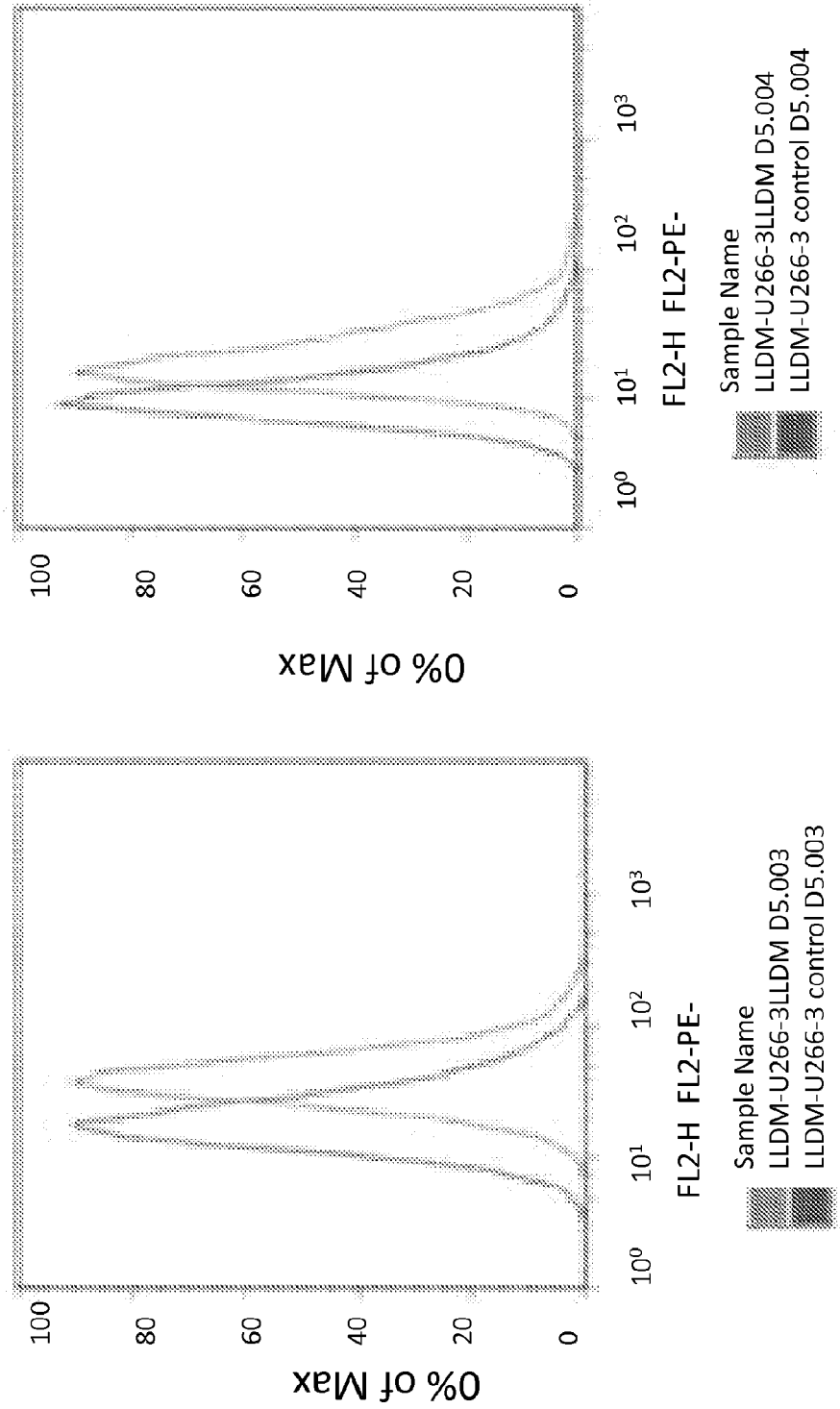
Figure 7:
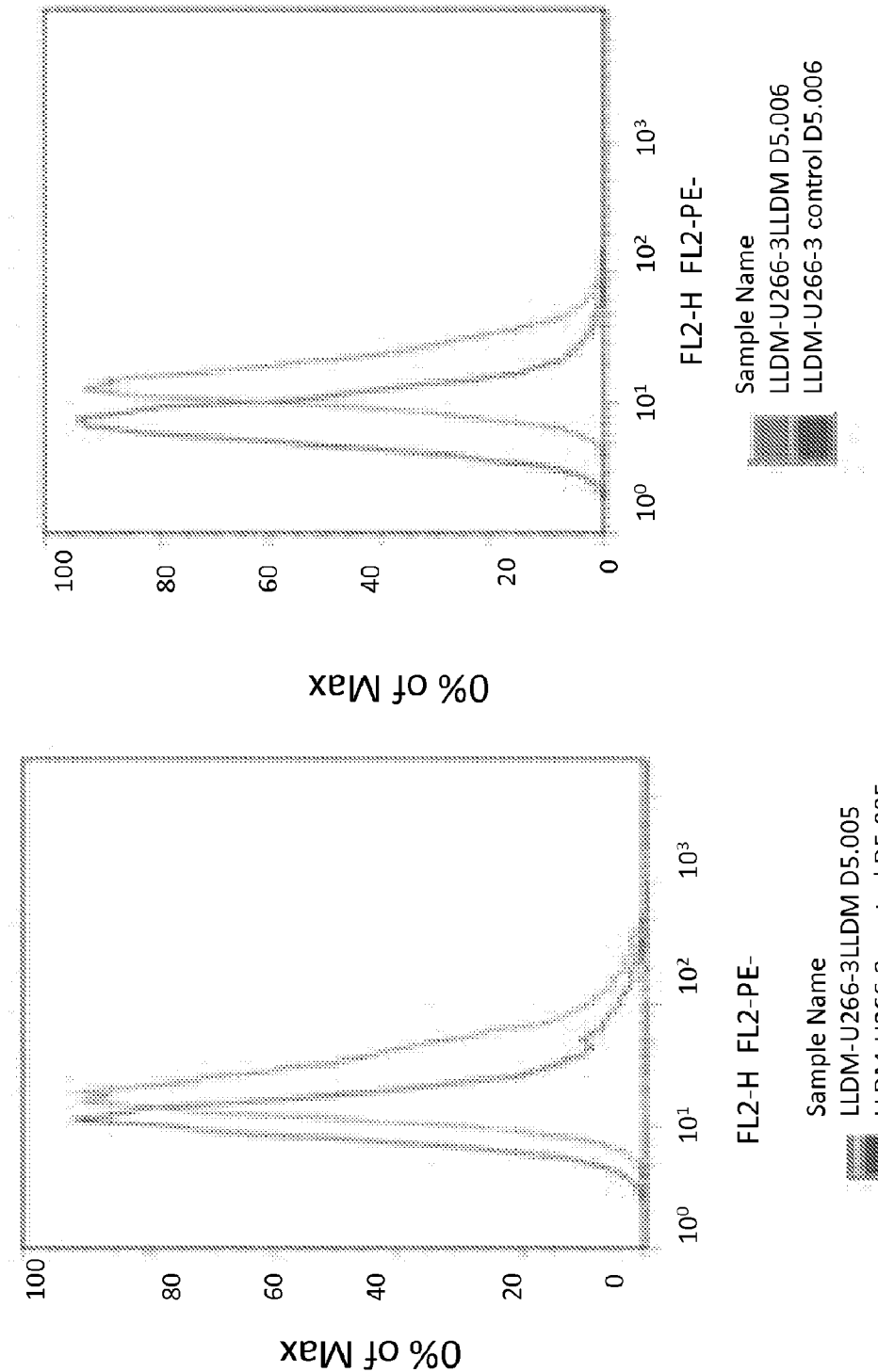
Figure 7:
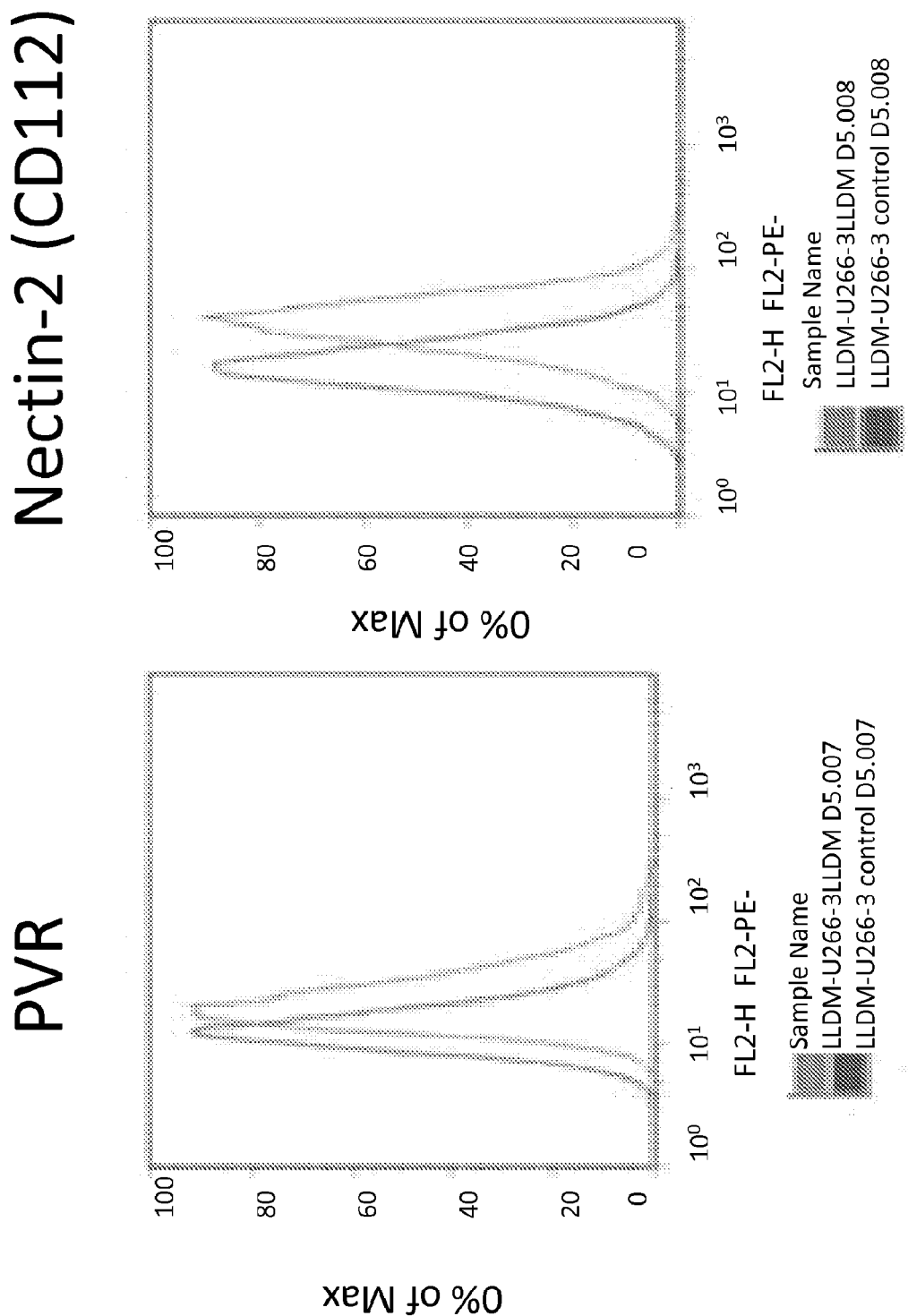

Referring now to FIG. 7. Results for a representative experiment showing that lenalidomide increases the expression of activating ligands on target cells. Briefly, U266 cells were cultured in complete medium in the presence or absence of lenalidomide (5 µM) for 5 days. U266 cells were then assayed by flow-cytometry for the level of expression of the activating ligands MICA, MICA/B, DR4, DR5, ULBP1, ULBP2, PVR and Nectin-2 (CD112) in U266 cells. As shown, lenalidomide enhanced the expression of the activating ligands to varying extents (see below).

Figure 8:
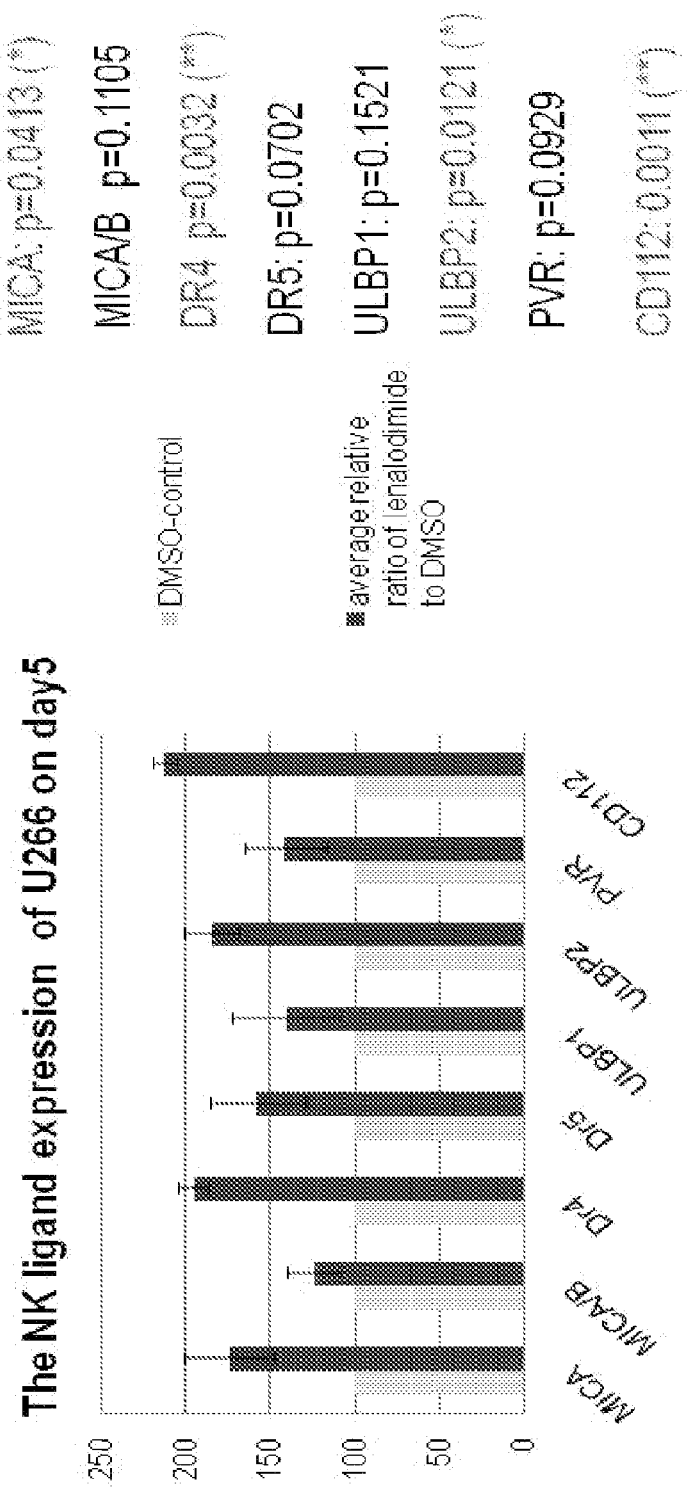
FIG. 8. Bar graph summarizing the effect of lenalidomide on the expression of activating ligands on U266 cells in at least 4 independent experiments.

Referring now to FIG. 8. Bar graph summarizing the effect of lenalidomide on the expression of activating ligands on U266 cells in at least 4 independent experiments. In this experiment U266 cells were analyzed as described as in the above. The data were analyzed using the paired t-test. In this experiment lenalidomide is shown to significantly increase the expression of only MICA, DR4, ULBP2, and CD112 on U266 cells. The data strongly suggest that lenalidomide enhances the susceptibility of U266 cells to NK cell mediated killing by increasing the expression of activating ligands. Consistent with these results lenalidomide significantly increases the expression of MICA, ULBP2, DR4, and CD112 on U266 cells.

Figure 9:
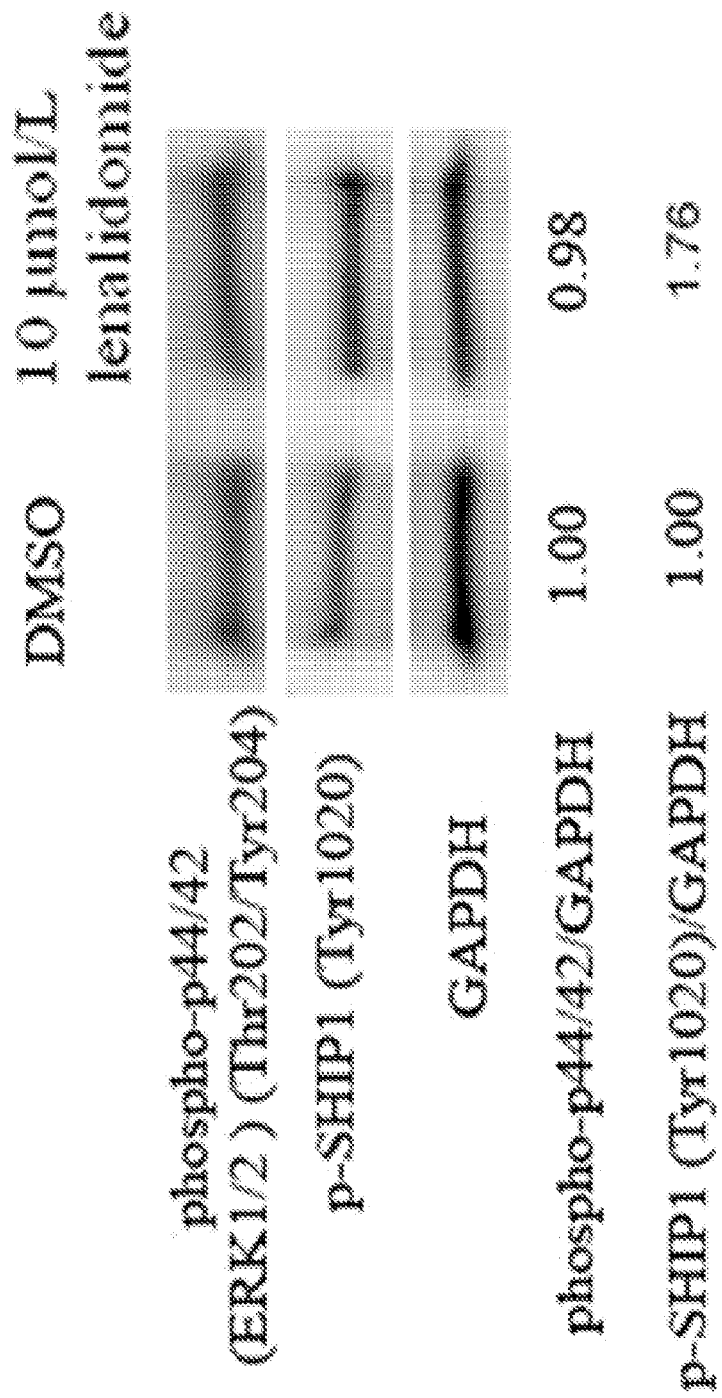
FIG. 9. Western blot analysis of cell lysates illustrating the effect of 10 μmolL$^{-1}$ lenalidomide versus DMSO on the expression of phospho-p44/42 (ERL1/2; Thr202/Tyr2040, pSHIP (Tyr1020). GAPDH is used as a protein loading control.

Referring now to FIG. 9. Western blot analysis was run on lysates of cells treated with either DMSO or 10 µmol/L. The gels were probed with antibodies to phospho p44/42 (Erk1/2) Thr202/Tyr204); p-SHIP1 (Tyr1020) and GAPDH, the antibodies were obtained from Cell Signaling Technology (Danvers, Mass. U.S.A.). The various bands were quantified by densitometry and the amounts of phospho-p44/42 (Erk1/2) Thr202/Tyr204) and p-SHIP1 (Tyr1020) were normalized to the amount of GAPDH measured in each lane. The values determined for phospho-p44/42 (Erk1/2) Thr202/Tyr204)/GAPDH measured from cells treated with either DMSO or 10 µmol/L lenalidomide were 1.00 and 0.98, respectfully. The values determined for P-SHIP1(Tyr1020)/GAPDH measured from cells treated with either DMSO or 10 µmol/L lenalidomide were 1.00 and 1.76, respectfully. Still referring to FIG. 9, these results indicate that lenalidomide may up-regulate the expression phospho-SHIP1 (Tyr1020) but it appears to have little or no effect on phospho-p44/42 (ERK1/2) (Thr202/Tyr204) expression in NK cells.

As described herein the monoclonal antibody 1-7F9 enhances the cytotoxicity of NK cells against myeloma cells in vitro. The combination of lenalidomide and 1-7F9 enhance NK cell mediated cytotoxicity against U266 cells beyond the results observed with each agent alone indicating a synergistic, or at least an additive effect. Lenalidomide increases the expression of activating NK cell receptor ligands on U266 cells and enhances the susceptibility of myeloma cell lines to NK cell based cytotoxicity in vitro. Lenalidomide may affect intracellular signaling pathway in NK cells, e.g., up-regulating the phospho-SHIP1 (Tyr1020) in NK cells.

Materials and Methods

Effector cells: PBMC and NK cells were collected from random donors. Target cells: The myeloma (MM) cell line U266 co-expresses class I and II HLA-C ligands. The K562 cell line is negative for HLA class I molecules and acts as negative control for 1-7F9 blocking experiment.

The Europium release cytotoxicity assay was performed according to the instruction of DELFIA® EuTDA Cytotoxicity AD0116 kit (PerkinElmer).

While the novel technology has been illustrated and described in detail in the figures and foregoing description, the same is to be considered as illustrative and not restrictive in character, it being understood that only the preferred embodiments have been shown and described and that al changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

I claim:

1. A method of treating a patient having a cancer, comprising administering to the patient a combination of a therapeutically effective amount of (a) 3-(4-amino-1-oxo-1,3 dihydroisoindol-2-yl)piperidine-2,6-dione or a pharmaceutically acceptable salt thereof, and (b) an antibody or an antigen-binding fragment thereof that (i) cross-reacts with KIR2DL1 and KIR2DL2/3, and (ii) enhances NK cell cytotoxicity.

2. The method according to claim 1, wherein the patient is a human.

3. The method according to claim 1, wherein the therapeutically effective amount of 3-(4-amino-1-oxo-1,3 dihydro-isoindol-2-yl)piperidine-2,6-dione or a pharmaceutically acceptable salt thereof is between about 1 mg to about 50 mg per day.

4. The method according to claim 1, wherein the therapeutically effective amount of 3-(4-amino-1-oxo-1,3 dihydro-isoindol-2-yl)piperidine-2,6-dione or a pharmaceutically acceptable salt thereof is between about 5 mg to about 50 mg per day.

5. The method according to claim 1, wherein the therapeutically effective amount of 3-(4-amino-1-oxo-1,3 dihydro-isoindol-2-yl)piperidine-2,6-dione or a pharmaceutically acceptable salt thereof is between about 1 mg to about 25 mg per day.

6. The method according to claim 1, wherein the therapeutically effective amount of said antibody or antigen-binding fragment thereof is between about 1 mg/kg to about 3 mg/kg per month.

7. The method according to claim 1, wherein the cancer is selected from chronic myeloid leukemia (CML), acute myeloid leukemia (AML), chronic lymphocytic leukemia (CLL), small lymphocytic lymphoma (SLL), and a myelodysplastic syndrome (MDS).

8. The method according to claim 1, wherein the antibody or antigen-binding fragment thereof comprises a light chain variable region having the amino acid sequence set forth in SEQ ID NO:1 and a heavy chain variable region having the amino acid sequence set forth in SEQ ID NO:2.

9. The method according to claim 1, wherein the antibody or antigen-binding fragment thereof comprises a light chain variable region having the amino acid sequence set forth in SEQ ID NO:1 and a heavy chain having the amino acid sequence set forth in SEQ ID NO:3.

10. A method of treating a patient having a cancer, consisting essentially of administering to the patient a combination of a therapeutically effective amount of (a) 3-(4-amino-1-oxo-1,3 dihydro-isoindol-2-yl)piperidine-2,6-dione or a pharmaceutically acceptable salt thereof and (b) an antibody or an antigen-binding fragment thereof that (i) cross-reacts with KIR2DL1 and KIR2DL2/3, and (ii) enhances NK cell cytotoxicity.

11. The method according to claim 10, wherein the cancer is selected from chronic myeloid leukemia (CML), acute myeloid leukemia (AML), chronic lymphocytic leukemia (CLL), small lymphocytic lymphoma (SLL), and a myelodysplastic syndrome (MDS).

12. The method according to claim 10, wherein the antibody or antigen-binding fragment thereof comprises a light chain variable region having the amino acid sequence set forth in SEQ ID NO:1 and a heavy chain variable region having the amino acid sequence set forth in SEQ ID NO:2.

13. The method according to claim 10, wherein the antibody or antigen-binding fragment thereof comprises a light chain variable region having the amino acid sequence set forth in SEQ ID NO:1 and a heavy chain having the amino acid sequence set forth in SEQ ID NO:3.

14. The method according to claim 1, wherein the combination elicits a synergistic or additive effect on NK cell-mediated killing of cancer cells.

15. The method according to claim 10, wherein the combination elicits a synergistic or additive effect on NK cell-mediated killing of cancer cells.

16. A kit for inducing death of cancer cells, comprising:
   a biologically active amount of 3-(4-amino-1-oxo-1,3 dihydro-isoindol-2-yl)piperidine-2,6-dione or a pharmaceutically acceptable salt thereof; and
   a biologically active amount of an antibody or an antigen-binding fragment thereof that (i) cross-reacts with KIR2DL1 and KIR2DL2/3, and (ii) enhances NK cell cytotoxicity.

17. A kit for treating a cancer, comprising:
   at least one therapeutically effective dose of 3-(4-amino-1-oxo-1,3 dihydro-isoindol-2-yl)piperidine-2,6-dione or a pharmaceutically acceptable salt thereof; and
   at least one therapeutically effective dose of an antibody or an antigen-binding fragment thereof that (i) cross-reacts with KIR2DL1 and KIR2DL2/3, and (ii) enhances NK cell cytotoxicity.

18. The kit according to claim 16, wherein the cancer is selected from chronic myeloid leukemia (CML), acute myeloid leukemia (AML), chronic lymphocytic leukemia (CLL), small lymphocytic lymphoma (SLL), and a myelodysplastic syndrome (MDS).

19. The kit according to claim 17, wherein the cancer is selected from chronic myeloid leukemia (CML), acute myeloid leukemia (AML), chronic lymphocytic leukemia (CLL), small lymphocytic lymphoma (SLL), and a myelodysplastic syndrome (MDS).

20. The kit according to claim 16, wherein the antibody or antigen-binding fragment thereof comprises a light chain variable region having the amino acid sequence set forth in SEQ ID NO:1 and a heavy chain variable region having the amino acid sequence set forth in SEQ ID NO:2.

21. The kit according to claim 17, wherein said antibody or antigen-binding fragment thereof comprises a light chain variable region having the amino acid sequence set forth in SEQ ID NO:1 and a heavy chain variable region having the amino acid sequence set forth in SEQ ID NO:2.

22. The kit according to claim 16, wherein the antibody or antigen-binding fragment thereof comprises a light chain variable region having the amino acid sequence set forth in SEQ ID NO:1 and a heavy chain having the amino acid sequence set forth in SEQ ID NO:3.

23. The kit according to claim 17, wherein the antibody or antigen-binding fragment thereof comprises a light chain variable region having the amino acid sequence set forth in SEQ ID NO:1 and a heavy chain having the amino acid sequence set forth in SEQ ID NO:3.

* * * * *